United States Patent [19]

Hoopman

[11] Patent Number: 5,454,951
[45] Date of Patent: Oct. 3, 1995

[54] SEPARATION-SCIENCE MEDIUM SUPPORT PLATE

[75] Inventor: Timothy L. Hoopman, River Falls, Wis.

[73] Assignee: Minnesota Mining and Manufacturing Company, St. Paul, Minn.

[21] Appl. No.: 27,079

[22] Filed: Mar. 5, 1993

[51] Int. Cl.⁶ .................................................. B01D 65/08
[52] U.S. Cl. ........................ 210/650; 210/321.84; 210/456
[58] Field of Search .......................... 210/321.6, 321.75, 210/321.84, 456, 446, 650

[56] References Cited

U.S. PATENT DOCUMENTS

| | | | |
|---|---|---|---|
| 3,209,915 | 10/1965 | Gutkowski | 210/347 |
| 3,361,261 | 1/1965 | Fairey et al. | 210/446 X |
| 3,386,585 | 11/1965 | Weyand et al. | 210/445 |
| 3,841,491 | 10/1974 | Hagstrom et al. | 210/321 |
| 3,929,648 | 12/1975 | Cuthbert | 210/446 X |
| 4,229,306 | 10/1980 | Hein et al. | 210/446 |
| 4,340,475 | 7/1982 | Kraus et al. | 210/321.84 X |
| 4,902,420 | 2/1990 | Pall et al. | 210/346 |
| 4,944,876 | 7/1990 | Miller | 210/321.75 |
| 5,100,551 | 3/1992 | Pall et al. | 210/346 |

FOREIGN PATENT DOCUMENTS

| | | |
|---|---|---|
| 3202330A1 | 9/1982 | Germany. |
| 558669 | 2/1975 | Switzerland. |

Primary Examiner—Frank Spear
Attorney, Agent, or Firm—Gary L. Griswold; Walter N. Kirn; Karl G. Hanson

[57] ABSTRACT

A separation-science medium support plate has a multiplicity of concentric, radially-spaced grooves located on an upstream side of the plate. The concentric, radially-spaced grooves each have two open ends that allow a groove to communicate, ultimately, with a radially-extending groove that has an opening located therein. The opening is disposed in the radially-extending groove towards the periphery of the support plate and allows a fluid to pass from the upstream side of plate to the downstream side. The plate lacks any openings for fluid passage other than the peripherally-located opening(s). A plate of this invention makes a centrally-deposited fluid droplet follow a highly tortuous path before passing through the peripherally-located opening(s), and this enables a separation-science membrane resting on the plate to become uniformly wet by the fluid.

19 Claims, 3 Drawing Sheets

SEPARATION-SCIENCE MEDIUM SUPPORT PLATE

TECHNICAL FIELD

This invention pertains to a plate which supports a separation science medium and allows for the even distribution of flow of a fluid through the medium.

BACKGROUND OF THE INVENTION

In the separation-science art, support plate's are known which are used for distributing a fluid uniformly over a separation-science medium. Examples of such known support plates are disclosed in the following U.S. Pat. Nos. 5,100,551; 4,944,876; 4,902,420; and 3,209,915. U.S. Pat. No. 4,944,876, in particular, discloses a support plate that has a recessed channel network for uniformly distributing a fluid across a membrane filter. The recessed channel network includes concentrically arranged circular channels and a plurality of radially extending channels that intersect with the circular channels and communicate with an outlet passage. The outlet passage is centrally located in the recessed channel network, and in this position does not allow a fluid that is deposited centrally on the membrane filter to become distributed over the peripheral portions of the filter. This can be problematic when the fluid inlet is also centrally located and the filter needs to be fully wetted.

SUMMARY OF THE INVENTION

The present invention provides a plate for supporting a separation science medium in such a manner that a fluid deposited centrally on the separation-science medium can become evenly distributed over the whole surface of the medium. The support plate is particularly effective for use in an apparatus which has a centrally located fluid inlet port. Briefly, the separation-science medium support plate of this invention comprises:

- a plate having a first and second opposite sides, the first side having a plurality of concentric radially-spaced grooves located thereon, the concentric radially-spaced grooves having first and second open ends which allow the concentric radially-spaced grooves to communicate with a groove (A) directly or via a groove (B),
- the groove (A) being a radially-extending groove that has an opening that allows a fluid to pass from the plate's first side to the plate's second side, the opening being disposed in the groove (A) at a peripheral end thereof, the groove (A) not permitting fluid passage from the plate's first side to plate's second side other than through the peripherally located opening,
- the groove (B) being a radially-extending groove that extends from a centrally-located, concentric groove towards a periphery of the plate to a concentric groove that communicates directly with the groove (A) at a first open end and directly with the groove (B) at a second open end.

The support plate of the invention has radially-extending grooves (A) that provide for fluid passage through the plate at peripherally-located openings rather than through a centrally-located passageway. The peripherally-located openings, in conjunction with the concentric, radially-spaced grooves and the radially-extending grooves (B), allow a fluid to become evenly distributed over the upstream side of the plate before passing through the support plate to the downstream side.

This and other advantages of the invention are more fully shown and described in the drawings and detailed description of this invention, where like reference numerals are used to represent similar parts. It is to be understood, however, that the description and drawings are for the purposes of illustration only and should not be read in a manner that would unduly limit the scope of this invention.

DETAILED DESCRIPTION OF THE PREFERRED EMBODIMENTS

In describing the preferred embodiments of the invention, specific terminology will be used for the sake of clarity. The invention, however, is not intended to be limited to the specific terms so selected, and it is to be understood that each term so selected includes all the technical equivalents that operate similarly.

Figure 1:
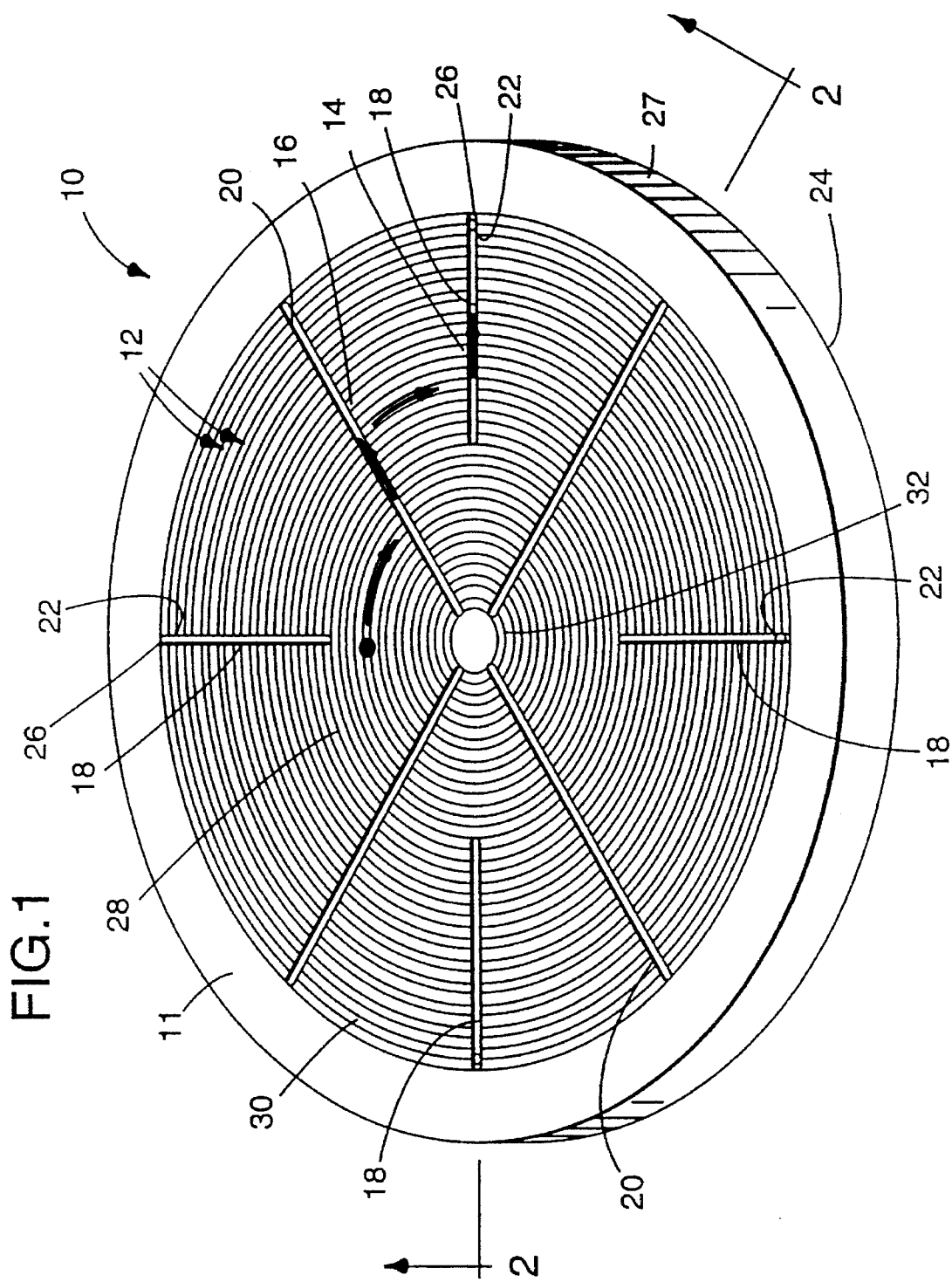
FIG. 1 is a perspective view of a separation-science medium support plate 10 in accordance with the present invention.
Figure 2:
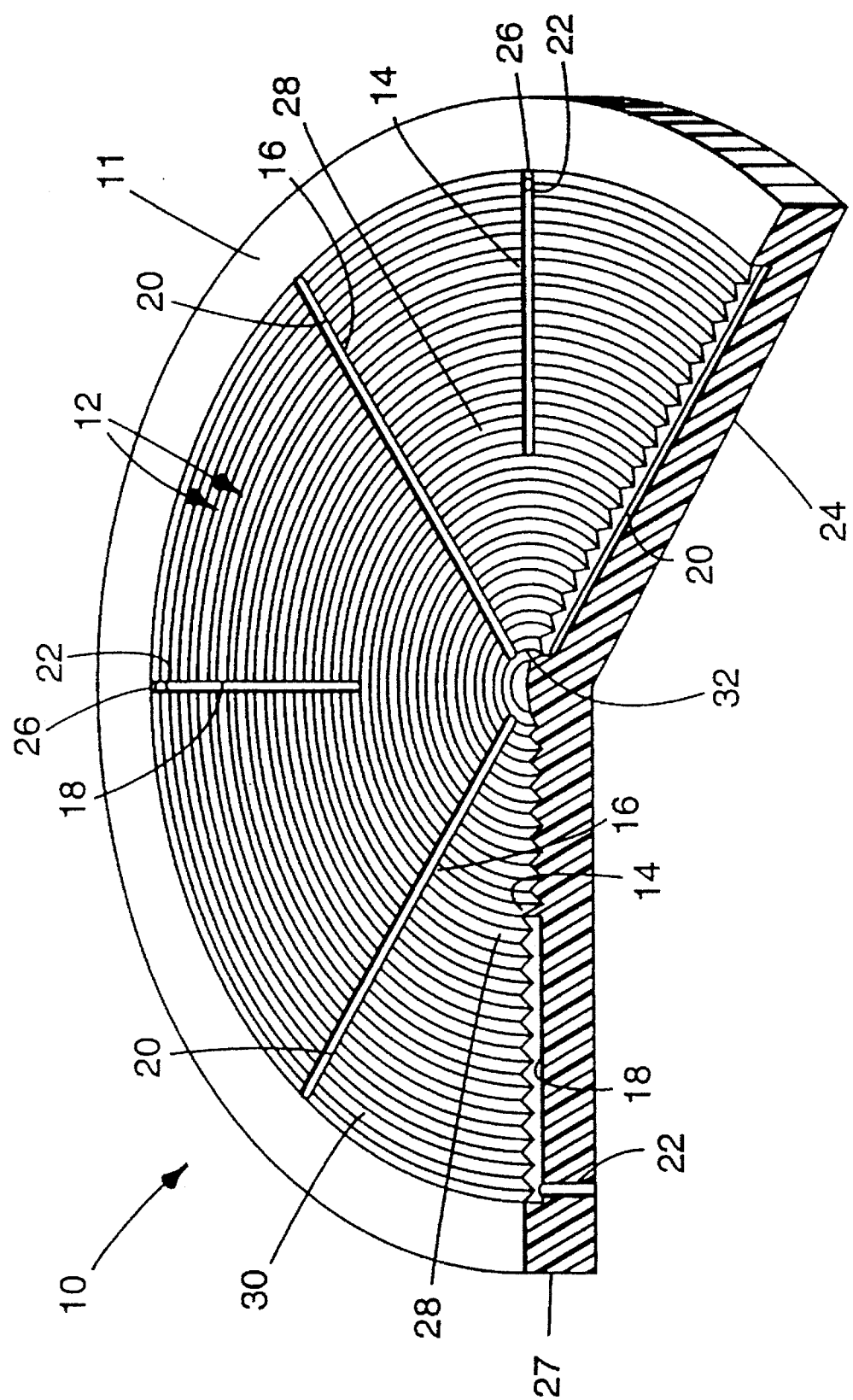
FIG. 2 is a sectional view taken along lines 2—2 of FIG. 1 of a separation-science medium support plate 10 in accordance with the present invention.

In the practice of the present invention, a separation-science medium support plate 10 is provided as shown in FIGS. 1 and 2 which has a plurality of concentric, radially-spaced grooves 12 located on a first or upstream side 11 of plate 10. The concentric, radially-spaced grooves 12 have first and second open ends 14 and 16 which allow the concentric, radially-spaced grooves 12 to communicate with either a groove (A) 18 or a groove (B) 20. The term "groove" means an elongate recess which does not fully penetrate the support plate.

Groove (A) 18 is a radially-extending groove that has an opening 22 which allows a fluid to pass from the plate's upstream side 11 to the plate's downstream side 24. Opening 22 is disposed in groove (A) 18 at a peripheral end 26. Opening 22 preferably is disposed in groove (A) 18 where it intersects with the most peripheral concentric groove. As best shown in FIG. 2, groove (A) 18 does not permit a fluid to pass from the plate's upstream side 11 to the downstream side 24 other than through the peripherally located opening 22. The peripherally-located openings 22 may be spaced inward from the outer edge 27 of plate 10 to prevent the obstruction of flow through the openings by a filter holder or housing onto which the plate 10 would normally rest on its edge during use, see, e.g., FIG. 3. The term "peripherally-located" means being disposed in the area occupied by the outer one-third number of the total number of concentric, radially-spaced grooves. The grooves (A) 18 preferably extend from a medially-located, concentric radially spaced groove 28 to a peripherally-located concentric, radially-spaced groove 30 and more preferably to the most peripherally-located concentric groove. The term "medially-located" means being disposed in the area occupied by the middle one-third number of concentric, radially-spaced grooves.

Groove (B) 20 is a radially-extending groove that extends from a centrally-located concentric groove 32 to a more medially-located concentric groove 28 that intersects with or communicates directly with groove (A) 18 at a first open end 14 and with groove (B) 20 at a second open end 16. The term "centrally-located" means being disposed in the area occupied by the central one-third number of concentric, radially-spaced grooves. Preferably, groove (B) extends from a centrally-located concentric groove 32 to a peripherally-located concentric groove 30, and more preferably from the most central concentric groove to the most peripheral concentric groove. Groove (B) 20 preferably does not have any openings located therein which would enable a fluid to pass from the plate's upstream side 11 to the downstream side 24. However, if a lower pressure drop is desired through plate 10, the peripheral end 26 of groove (B) 20 may have an opening (not shown) disposed therein to allow the passage of fluid from the plate's upstream side 11 to the plate's downstream side 24.

The concentric, radially-spaced grooves 12 and the radially-extending grooves (A) 18 and (B) 20 are so arranged on the first side 11 of the support plate 10 that the concentric, radially-spaced grooves 12 communicate with groove (A) 18 either directly or via groove (B) 20. Stated another way, a fluid which is deposited in the concentric, radially-spaced grooves 12 on the upstream side 11 of fluid distribution plate 10 passes to groove (A) 18 by traveling directly to groove (A) 18, or the fluid may pass from a first concentric, radially-spaced groove, to a groove (B) 20, to a second concentric, radially-spaced groove, and then to a groove (A) 18. The arrows in FIG. 1 illustrate how a fluid can pass to a groove (A) 18 via a groove (B) 20. Upon entering groove (A) 18, the fluid travels towards the peripheral end of groove (A) 18 to pass out the opening 22. The path taken for a fluid to arrive at groove (A) 18 depends on the original location of the fluid on the support plate. For example, a centrally-deposited fluid droplet will arrive at groove (A) 18 via a tortuous route through a centrally-located concentric, radially-spaced groove 32, to groove (B) 20, to a more medially-located concentric, radially-spaced groove 28, and then to groove (A) 18. In contrast, a peripherally-deposited fluid droplet would pass directly to groove (A) 18 and out opening 22.

The number of concentric, radially-spaced grooves 12 may vary depending the particular use of the support plate. For example, a support plate used in a hypodermic syringe to support a separation-science medium may have as few as three concentric radially-spaced grooves; whereas in a commercial scale water treatment plant there may be a multiplicity (for example, greater than 20) or legions (for example, greater than 100) of concentric, radially-spaced grooves 12 and a plurality or multiplicity of grooves (A) 18 and grooves (B) 20. Typically there will be at least three grooves (A) and three grooves (B) in an alternating radial arrangement. The support plate 10 preferably does not possess any centrally or medially disposed openings through which a fluid can pass to the downstream side of the plate. That is, in a preferred embodiment, the only openings through which a fluid can pass to the downstream side 24 of plate 10 are the peripherally-located openings 22 in grooves (A) 18, and possibly in grooves (B) 20.

The concentric grooves 12 may take on a variety of cross-sectional configurations, for example, semi-circular, trapezoidal, V-shaped, etc. Preferred concentric, radially-spaced grooves 12 have a keen edge on the peaks separating the grooves. The provision of a keen edge between the grooves minimizes the contact area with a separation-science medium that rests on the upstream side 11 of plate 10. The V-shaped grooves best shown in FIG. 2 are an example of grooves which have a generally keen edge to minimize contact area. The minimization of contact area with the separation-science medium maximizes the useful surface through which a fluid may pass, and also minimizes fluid retention on the upstream side 11 of plate 10 to allow for quick displacement of a fluid through plate 10.

The present invention may be suitable for use with virtually any separation-science medium. The term "separation-science medium" means any item, such as a filter, membrane, or other medium or combination of media, which is used in the scientific, and especially the chemical and biological fields, in the art of separation, isolation, purification, identification, and the like or combinations thereof. Separation-science media include: any presently known or later developed filters; solid-phase extraction (SPE) membranes or disks including Empore™ extraction disks available from 3M Company (Saint Paul, Minn.) and Nuclepore™ Filinert™ membranes available from Nuclepore Company (Pleasanton, Calif.); and cellulosic membranes comprised of cellulose acetate and cellulose nitrate such as Membra-fil™ also available from Nuclepore™. A particularly preferred SPE membrane comprises a polytetrafluoroethylene (PTFE) fibril matrix having nonswellable, hydrophobic, sorptive particles enmeshed therein such as disclosed in U.S. Pat. Nos. 5,147,539; 5,071,610; 4,971,736; 4,906,378; and 4,810,381; and WO 93/00163, the disclosures of which are incorporated here by reference.

When a membrane, particularly a relatively thin membrane, is used as a separation-science medium, the spacing between the concentric, radially-spaced grooves preferably is sufficiently small to prevent the membrane from deforming into and restricting flow through the concentric radially-spaced grooves. Thin membranes have a tendency to sag into the groove to assume the cross-sectional configuration of the groove. By limiting the spacing between the concentric, radially-spaced grooves 12, the membrane sagging problem can be averted. Thus, the concentric, radially-spaced grooves 12 are spaced less than the thickness of the separation-science membrane, and in some instances the spacing may be at most one-half or one-fourth the thickness of a separation-science membrane. It is also preferred that grooves (A) 18 and (B) 20 each have a width that is sufficiently small to prevent the separation-science medium from deforming into the radially-spaced grooves.

When a thin membrane is used as a separation-science medium, for example, an Empore" disk membrane which has a thickness on the order of 500 to 550 micrometers, it is preferred that the concentric, radially-spaced grooves are microgrooves, which are grooves that have a center-to-center spacing of less than approximately 500 micrometers, more preferably less than 400 micrometers, and more preferably in the range of 200 to 375 micrometers. The concentric, radially-spaced microgrooves preferably have a depth in the range of 200 to 900 micrometers, more preferably in the range of 350 to 500 micrometers. The depth of the concentric grooves and radially-spaced grooves may vary depending on the desired rate of flow through the SPE medium.

Figure 3:
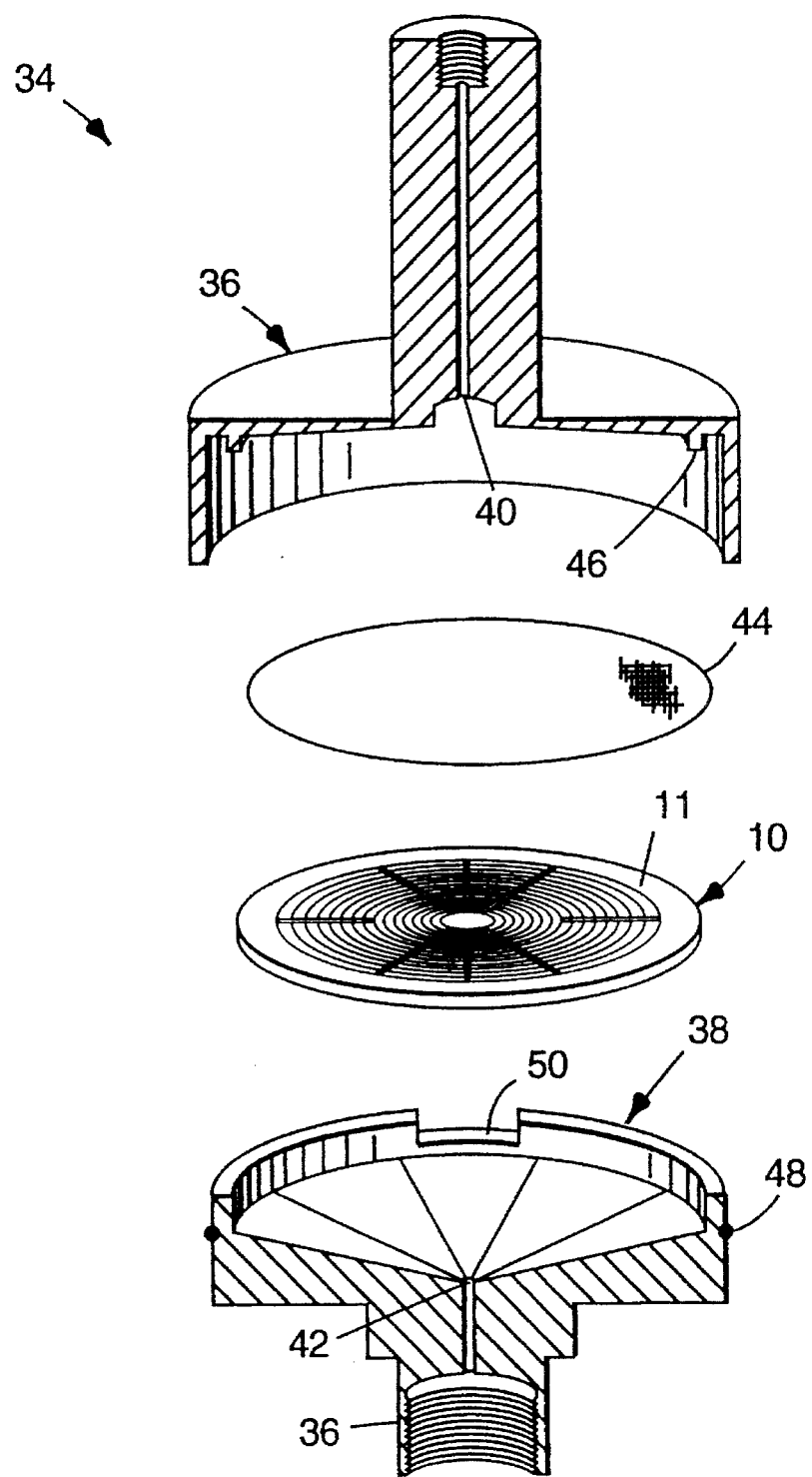
FIG. 3 illustrates a separation-science medium support plate 10 disposed in a housing 34 in accordance with the present invention.

FIG. 3 illustrates a support plate 10 in a housing 34. Housing 34 includes a first-half 36 and a second-half 38. A fluid enters housing 34 by passing through inlet 40 in first-half 36, and exits the housing 34 by passing through outlet 42 in the second-half 38. A separation-science medium 44 is disposed on the upstream side 11 of support plate 10. An annular flange 46 can project from the first-half of housing 36 to insure that fluid travelling from inlet 40 to outlet 42 passes through the separation-science medium 44.

When the first-half 36 is joined to the second-half 38, annular flange 46 forces the separation-science medium 44 against the support plate 10 along the periphery of the separation-science medium. An O-ring 48 can be provided to allow the first-half 36 to become hermetically joined to the second-half 38 of housing 34. A fluid can then be forced through the housing 34 under pressurized conditions. A cut-out portion 50 may be provided in second-half 38 to facilitate removal of the separation-science medium 44 from housing 34.

When a fluid passes from inlet 40 into the interior of housing 34, it will generally be deposited centrally on the separation-science medium 44. By use of the support plate 10, however, the centrally-deposited fluid can become distributed evenly over the whole surface of the separation-science medium 44. This allows the fluid to fully wet the separation-science medium 44 and enables the whole surface of medium to be used in a filtration or an extraction. When a hydrophobic separation-science medium is employed, such as a PTFE fibril matrix having hydrophobic sorptive particles enmeshed therein, it is important that the whole surface of the membrane becomes wetted with fluid. Otherwise, certain portions of the membrane can make contact with air which can dry out that portion of the membrane and prevent the flow of fluid therethrough. A support plate 10 of this invention helps to alleviate this problem; see U.S. application Ser. No. 08/027,880, filed the same day as this application by Richard M. Pieper et at.

Features and advantages of this invention are further illustrated in the following example. It is to be expressly understood, however, that while the example serves this purpose, the particular ingredients and amounts used as well as other conditions and details are not to be construed in a manner that would unduly limit the scope of this invention.

EXAMPLE

A housing was designed for use with Empore™ disks that were 47 millimeters (ram) in diameter and 0.5 mm thick, available from Varian Sample Preparation Products, Harbour, Calif. The housing had an inside diameter of 48 ram, and a chamber was disposed above the Empore™ disk in the housing which was 45 mm in diameter and 30 mm high. The disk was placed on a support plate having a construction similar to the support plate shown in FIGS. 1 and 2. The support plate was a plastic disk machined from a piece of Kel-F™ Brand polychlorotrifluoroethylene (PCTFE) thermoplastic available from 3M Company, Industrial Chemical Products. The support plate had approximately 86 concentric, radially-spaced grooves on the upstream side of the support plate. There were approximately 4 grooves per millimeter which were about 0.28 mm deep. In addition to the concentric grooves, radially-extending grooves were machined into the upstream surface of the support plate in the pattern shown in FIGS. 1 and 2. Each radially-extending groove was approximately 0.5 mm wide and 0.5 to 0.75 mm deep. A vent, constructed of a plugged tube fitting 6 mm in diameter was built into the top of the chamber. The vent could be opened (vented) and closed as needed.

The purpose of this Example was to determine if a water solution containing a blue dye would pass uniformly through a primed solid-phase extraction membrane.

The membrane was primed with 10 milliliters (ml) of methanol while the vent was left open, allowing the disk to be immersed in methanol. The vent was then closed, and the membrane was further primed with an additional 10 ml of methanol. Then 10 ml of water were pumped into the housing to displace the methanol, and a 100 ml sample of water containing a blue dye was pumped through the membrane. The dye was an Alphazurine A dye, lot CZ01712CZ, available from Aldrich Chemical Company, Inc., Milwaukee, Wis. The membrane remained completely and continuously immersed in liquid throughout the procedure. At the end of the procedure, a blast of high pressure air forced all of the liquid through the membrane. Upon visual examination, the blue dye was seen to be evenly distributed over the entire surface of the membrane, thereby demonstrating uniform flow through the membrane using the support plate of this invention.

This invention may take on various modifications and alterations without departing from the spirit and scope thereof. Accordingly, it is to be understood that this invention is not to be limited to the above-described, but is to be controlled by the limitations set forth in the following claims and any equivalents thereof. It is also to be understood that this invention may be suitably practiced in the absence of any element not specifically disclosed herein.

What is claimed is:

1. A separation-science medium support plate that comprises:

a plate having a first and second opposite sides, the first side having a plurality of concentric radially-spaced grooves located thereon, the concentric radially-spaced grooves having first and second open ends which allow the concentric radially-spaced grooves to communicate with a groove (A) directly or via a groove (B), the groove (A) being a radially-extending groove that has a first end that intersects with a medially-located concentric groove and that has an opening that allows a fluid to pass from the plate's first side to the plate's second side, the opening being disposed in the groove (A) at a peripheral end thereof, the groove (A) not permitting fluid passage from the plate's first side to plate's second side other than through the peripherally located opening, the groove (B) being a radially-extending groove that extends from a centrally-located, concentric groove to a peripherally-located concentric groove that communicates directly with the groove (A) at a first open end and directly with the groove (B) at a second open end.

2. The separation-science medium support plate of claim 1, wherein the groove (A) extends from a medially-located, concentric, radially-spaced groove to a peripherally-located, concentric, radially-spaced groove.

3. The separation-science medium support plate of claim 1, wherein a centrally-deposited fluid droplet passes through the outlet in the groove (A) by passing through a centrally-located, concentric, radially-spaced groove to the groove (B), to a second concentric, radially-spaced groove, to groove (A), and then through the opening in the groove (A).

4. The separation-science medium support plate of claim 3, wherein a peripherally-deposited fluid droplet passes from a peripherally-located concentric radially-spaced groove directly to the groove (A).

5. The separation-science medium support plate of claim 1, wherein there are greater than 20 concentric, radially-spaced grooves on the first side of the plate.

6. The separation-science medium support plate of claim 5, wherein there are greater than 100 concentric, radially-spaced grooves on the first side of the plate.

7. The separation-science medium support plate of claim 1, wherein there are at least three grooves (A) and at least three grooves (B) in an alternating radial arrangement on the first side of the plate.

8. The separation-science medium support plate of claim 1 wherein the only openings through which a fluid can pass to the downstream side of the plate are the peripherally-located openings in the grooves (A).

9. The separation-science medium support plate of claim 1, wherein the concentric, radially-spaced grooves have a keen edge at the peak separating the concentric, radially-spaced grooves.

10. A separation-science medium assembly, which comprises a solid-phase extraction membrane disposed on the first side of the separation-science medium support plate of claim 1.

11. The assembly of claim 10, wherein the solid-phase extraction membrane is a polytetrafluoroethylene fibril matrix having sorptive particles enmeshed therein.

12. The assembly of claim 10, wherein the support plate is disposed in a pressurizable housing having an inlet and an outlet, the solid-phase extraction membrane being disposed in the pressurizable housing such that a fluid traveling from the inlet to the outlet passes through the solid-phase extraction membrane.

13. The assembly of claim 12, wherein the inlet is centrally located over the solid-phase extraction membrane.

14. The assembly of claim 13, wherein the separation-science medium is a polytetrafluoroethylene fibril matrix having sorptive particles enmeshed therein.

15. The assembly of claim 12, wherein the concentric, radially-spaced grooves have a center-to-center spacing of less than 500 micrometers and have a depth in the range of 200 to 900 micrometers.

16. A method of performing a solid-phase extraction, which comprises passing a fluid through a solid-phase extraction membrane resting upon the support plate of claim 1.

17. A separation-science medium support plate that comprises:

a plate having first and second opposite sides, the first side having (i) a plurality of concentric, radially-spaced grooves located thereon which have first and second open ends and (ii) at least one radially-extending groove (A) and at least one radially-extending groove (B), at least one of the plurality of concentric, radially-spaced grooves intersecting at the first open end with the radially-extending groove (A) and at the second open end with the radially-extending groove (B), and at least one of the plurality of concentric, radially-spaced grooves intersecting at the first and second open ends only with the at least one radially-extending groove (B), the at least one radially-extending groove (A) extending from a medially-located concentric groove to a peripherally-located concentric groove, and the at least one radially-extending groove (B) extending from a centrally-located concentric groove to a peripherally-located concentric groove which intersects with the at least one groove (A) at the first open end, the at least one radially-extending groove (A), the at least one radially-extending groove (B), or both the radially-extending grooves (A) and (B) having an opening disposed therein to allow a fluid to pass from the plate's first side to the plate's second side.

18. A separation-science medium support plate that comprises:

a plate having a first and second opposite sides, the first side having a plurality of concentric radially-spaced grooves located thereon, the concentric radially-spaced grooves having first and second open ends which allow the concentric radially-spaced grooves to communicate with a groove (A) directly or via a groove (B), the groove (A) being a radially-extending groove that has a first end that intersects with a medially-located concentric groove and that has an opening that allows a fluid to pass from the plate's first side to the plate's second side, the opening being disposed in the groove (A) at a peripheral end thereof, the groove (A) not permitting fluid passage from the plate's first side to plate's second side other than through the peripherally located opening, the groove (B) being a radially-extending groove that extends from a centrally-located, concentric groove towards a periphery of the plate to a concentric groove that communicates directly with the groove (A) at a first open end and directly with the groove (B) at a second open end, wherein groove (B) does not have any openings located therein which would allow a fluid to pass from the plate's first side to the plate's second side.

19. A separation-science medium support plate that comprises:

a plate having a first and second opposite sides, the first side having a plurality of concentric radially-spaced grooves located thereon, the concentric radially-spaced grooves having first and second open ends which allow the concentric radially-spaced grooves to communicate with a groove (A) directly or via a groove (B), the groove (A) being a radially-extending groove that has a first end that intersects with a medially-located concentric groove and that has an opening that allows a fluid to pass from the plate's first side to the plate's second side, the opening being disposed in the groove (A) at a peripheral end thereof, the groove (A) not permitting fluid passage from the plate's first side to plate's second side other than through the peripherally located opening, the groove (B) being a radially-extending groove that extends from a centrally-located, concentric groove towards a periphery of the plate to a concentric groove that communicates directly with the groove (A) at a first open end and directly with the groove (B) at a second open end, wherein the plate does not possess any centrally or medially located openings through which a fluid can pass to a downstream side of the plate.

* * * * *

UNITED STATES PATENT AND TRADEMARK OFFICE
CERTIFICATE OF CORRECTION

PATENT NO.: 5,454,951

DATED: October 3, 1995

INVENTOR(S): Timothy L. Hoopman

It is certified that error appears in the above-identified patent and that said Letters Patent is hereby corrected as shown below:

Col. 1, line 13, "plate's" should be --plates--.

Col. 4, line 46, "Empore"" should be --Empore™--.

Col. 5, line 27, "08/027,880" should be --08/027,080--.

Col. 5, line 39, "(ram)" should be --(mm)--.

Col. 5, line 41 "ram," should be --mm,--.

Col. 5, line 47, "polychlorotrifiuoroethylene" should be --polychlorotrifluoroethylene--.

Signed and Sealed this

Sixteenth Day of January, 1996

Attest:

BRUCE LEHMAN

*Attesting Officer*       Commissioner of Patents and Trademarks